(12) United States Patent
Badoz et al.

(10) Patent No.: US 7,740,480 B2
(45) Date of Patent: Jun. 22, 2010

(54) SEQUENCE OF CANAL INSTRUMENTS FOR EXECUTING AN ENDODONTIC OPERATIVE PROCEDURE

(75) Inventors: Jean-Marie Badoz, Doubs (FR); Hubert Euvrard, Besançon (FR); Paul Calas, Toulouse (FR); Jean-Marie Vulcain, Vitre (FR)

(73) Assignee: Micro Mega International Manufactures, Besancon (FR)

( * ) Notice: Subject to any disclaimer, the term of this patent is extended or adjusted under 35 U.S.C. 154(b) by 966 days.

(21) Appl. No.: 10/416,630

(22) PCT Filed: Oct. 8, 2001

(86) PCT No.: PCT/FR01/03092

§ 371 (c)(1),
(2), (4) Date: May 14, 2003

(87) PCT Pub. No.: WO02/43607

PCT Pub. Date: Jun. 6, 2002

(65) Prior Publication Data

US 2004/0014003 A1    Jan. 22, 2004

(30) Foreign Application Priority Data

Nov. 29, 2000    (FR) ................................. 00 15388

(51) Int. Cl.
*A61C 5/02*    (2006.01)

(52) U.S. Cl. ...................................................... 433/102

(58) Field of Classification Search .................. 433/102, 433/224, 81, 165
See application file for complete search history.

(56) References Cited

U.S. PATENT DOCUMENTS

| 4,611,508 | A |   | 9/1986  | Roane              |         |
|-----------|---|---|---------|--------------------|---------|
| 5,380,200 | A |   | 1/1995  | Heath et al.       |         |
| 5,588,835 | A |   | 12/1996 | Kert               |         |
| 5,653,590 | A | * | 8/1997  | Heath et al.       | 433/102 |
| 5,658,145 | A |   | 8/1997  | Maillefer et al.   |         |
| 5,676,541 | A | * | 10/1997 | Maillefer et al.   | 433/102 |
| 5,857,852 | A |   | 1/1999  | Garman             |         |
| 5,897,316 | A | * | 4/1999  | Buchanan           | 433/102 |
| 6,293,794 | B1|   | 9/2001  | McSpadden          |         |

FOREIGN PATENT DOCUMENTS

| DE | 19852931   | 3/2000  |
|----|------------|---------|
| EP | 0501255    | 9/1992  |
| EP | 0684019    | 11/1995 |
| EP | 0780100    | 6/1997  |
| WO | WO 9314714 | 8/1993  |

* cited by examiner

*Primary Examiner*—Cris L Rodriguez
*Assistant Examiner*—Michael R Ballinger
(74) *Attorney, Agent, or Firm*—Gary M. Cohen

(57) ABSTRACT

A sequence of canal instruments for performing an endodontic operating protocol uses a sequence of several instruments, for example, three such instruments with three cutting blades. The instruments have a progressive conicity, for example, 6%, 4% and 2%, and each instrument has an identical progressive pitch. The pitch further increases progressively from instrument to instrument as a function of the conicity of each instrument.

6 Claims, No Drawings

SEQUENCE OF CANAL INSTRUMENTS FOR EXECUTING AN ENDODONTIC OPERATIVE PROCEDURE

BACKGROUND OF THE INVENTION

The present invention relates to a sequence of canal instruments for performing an endodontic operating protocol using a sequence of several instruments, for example, a sequence of three such instruments with three cutting blades.

Sequences of canal instruments of this type are known. Instruments with progressive pitch are such that the pitch of the instrument increases from the apex toward the handle. The progressive pitch of the instrument prevents the instrument from being screwed into the tooth resulting continued rotation.

The increase in pitch leads to a reduction in the residual core of the instrument, in this way increasing its reliability. This provides an acceptable flexibility for a conicity of 2%. However, as the conicity increases, the flexibility is progressively reduced.

SUMMARY OF THE INVENTION

In accordance with the present invention, this problem is solved by providing a sequence of canal instruments for performing an endodontic operating protocol using a sequence of several instruments, for example, a sequence of three such instruments with three cutting blades. The instruments have a progressive conicity, and each instrument has an identical progressive pitch. The pitch of the instruments increases progressively as a function of the conicity of the instrument.

DETAILED DESCRIPTION OF THE INVENTION

A sequence of canal instruments is provided for performing an endodontic operating protocol using a sequence of several instruments, for example, a sequence of three such instruments with three cutting blades. The instruments have a progressive conicity, and each instrument has an identical progressive pitch. The pitch of the instruments increases progressively as a function of conicity of the instrument. Advantageously, this progressive conicity will be 6%, 4% and 2%.

As an example, but without limitation, such a sequence of instruments can include an instrument having a conicity of 2% and a pitch x, an instrument having a conicity of 4% and a pitch 1.5x, and an instrument having a conicity of 6% and a pitch 2x. The progression of the pitch of each instrument increases from the apex (tip) of the instrument to the handle.

In certain cases, such as simple canals, this makes it possible to simplify the operating sequence by omitting one canal instrument. For example, an instrument with a conicity of 4% can be brought as far as the apex.

The invention claimed is:

1. A sequence of canal instruments for performing an endodontic operating protocol comprising a plurality of instruments adapted for use in a defined sequence, wherein each of the instruments has a plurality of cutting blades, wherein the sequence of instruments have progressive conicities from instrument to instrument in the sequence, wherein the sequence of instruments have progressive pitches including a defined progression and a defined initial pitch, wherein the progression of each instrument is identical to the progression of the other instruments in the sequence, and wherein the initial pitch of the instruments in the sequence of instruments increases progressively as a function of the conicities of the instruments in the sequence and varies in increasing proportion.

2. The sequence of canal instruments of claim 1 which includes a series of three instruments.

3. The sequence of canal instruments of claim 1 wherein each of the instruments has three cutting blades.

4. The sequence of canal instruments of claim 1 wherein the sequence of instruments includes a first instrument having a conicity of 6%, a second instrument having a conicity of 4% and a third instrument having a conicity of 2%.

5. The sequence of canal instruments of claim 4 wherein the third instrument has a defined initial pitch, the second instrument has a defined initial pitch which is 1.5 times the defined initial pitch of the third instrument, and the first instrument has a defined initial pitch which is 2 times the defined initial pitch of the third instrument.

6. The sequence of canal instruments of claim 1 wherein each of the instruments includes an apex at one end and a handle at another end, and wherein the pitch of each instrument progressively increases from the apex to the handle.

* * * * *